United States Patent [19]
Connors et al.

[11] Patent Number: 5,958,682
[45] Date of Patent: *Sep. 28, 1999

[54] BACTERIAL NITROREDUCTASE GENE-PRODRUG SYSTEM

[75] Inventors: Thomas Connors, Carshalton; Richard Knox, Belmont Sutton; Roger Sherwood, Salisbury, all of United Kingdom

[73] Assignee: Cancer Research Campaign Technology Limited, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/640,808

[22] PCT Filed: Nov. 4, 1994

[86] PCT No.: PCT/GB94/02423

§ 371 Date: Jul. 1, 1996

§ 102(e) Date: Jul. 1, 1996

[87] PCT Pub. No.: WO95/12678

PCT Pub. Date: May 11, 1995

[30] Foreign Application Priority Data

Nov. 5, 1993 [GB] United Kingdom .................... 9323008

[51] Int. Cl.$^6$ .............................. C12N 5/00; C12N 15/00; C07H 21/04
[52] U.S. Cl. .......................... 435/6; 435/320.1; 435/325; 435/455; 536/23.7
[58] Field of Search .......................... 514/44; 435/240.2, 435/320.1; 935/62

[56] References Cited

FOREIGN PATENT DOCUMENTS

93/08288  4/1993  WIPO .
93/11099  6/1993  WIPO .

OTHER PUBLICATIONS

J. Bridgewater et al., Euro. J. of Cancer, vol. 31A, No.s 13/14, pp. 2362–2370, 1995.
S. Bailey et al., Gene Therapy, vol. 3, pp. 1143–1150, 1996.
M. Ford et al., 2nd European Conference on Gene Therapy of Cancer, London, Sep. 7–8, 1995, Abstract 56.
J. Roth et al., Nature Medicine, vol. 2, No. 9, pp. 985–991, 1996.
E. Borrelli et al., Proc. Natl. Acad. Sci. USA, vol. 85, pp. 7572–7576, 1996.
T. Friedmann, Annals of Medicine, vol. 24, pp. 411–417, 1992.
F. Moolton, Human Gene Therapy, vol. 1, pp. 125–134, 1990.
Bailey et al (1996) Gene Therapy 3, 1143–1150.
Mullen (1994) Pharmac. Ther. 63, 199–207.
E. Marshall (1995) Science 269:1050–1055.
Vile et al (1995) Targeted Gene Therapy 9:190–199.
Culver et al (1992) Science 256: 1550–1552.
RAM, Zvi et al., "In Situ Retrroviral–mediated Gene Transfer for the Treatment of Brain Tumors in Rats," *Cancer Research*, vol. 53, pp. 83–88 (1993).
Engelhardt, John F. et al., "Direct Gene Transfer of Human CFTR into Human Bronchial Epithelia of Xenografts with E1–deleted Adenoviruses," *Nature Genetics*, vol. 4, pp. 27–34 (1993).
Knox, Richard J. et al., "The Bioactivation of 5–(Aziridin–1–YL)–2,4–Dinitrobenzamide (CB1954)–II," *Bio–chemical Pharmacology*, vol. 44, No. 12, pp. 2297–2301, (1992).
Knox, Richard J. et al., "Bioactivation of CB 1954: Reaction of the Active 4–Hydroxylamino Derivative with Thioesters to Form the Ultimate DNA–DNA Interstrand Crosslinking Species," *Biochemical Pharmacology*, vol. 42, pp. 1691–1697, (1991).
Mauger, Anthony B. et al., "Self–Immolative Prodrugs: Candidates for Antibody–Directed Enzyme Prodrug Therapy in Conjunction with a Nitroreductase Enzyme," *J. Med. Chem.*, vol. 37, pp. 3452–3458, (1994).

*Primary Examiner*—Deborah Crouch
*Attorney, Agent, or Firm*—Venable; John W. Schneller; Lawrence J. Carroll

[57] ABSTRACT

A system is disclosed which comprises: (i) a viral vector comprising a nucleotide sequence encoding a nitroreductase, which nitroreductase is capable of converting a prodrug into a cytotoxic drug; and (ii) a prodrug capable of being converted into a cytotoxic drug by the nitroreductase encoded by the vector. The disclosed invention also includes methods for killing cancerous and/or non-cancerous cells using the system described above. Included in the invention are methods for killing cells in vitro by introducing a vector encoding a nitroreductase into the cells, and then by providing a prodrug to the cells growing in vitro. Also included are methods in which cancerous and/or non-cancerous cells are killed in vivo in an animal or human by administering the vector and prodrug directly to cells of the animal or human. The invention further includes methods in which cancerous and/or non-cancerous cells are killed in vivo in an animal or human, by introducing a viral vector encoding a nitroreductase into animal or human cells growing in vitro so that the nitroreductase is produced in the cells, administering the cells to an animal or human subject, and then administering a prodrug to the animal or human, where it is converted into a cytotoxic agent in nitroreductase-containing cells of the animal or human.

14 Claims, 5 Drawing Sheets

▲ PRODRUG
▼ + 2μg/mL NR
♦ + 5μg/mL NR
✱ + 10μg/mL NR
■ ActinomycinD

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1167 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: B (ix) FEATURE:
        (A) NAME/KEY: CDS
        (B) LOCATION: 176..829

(xi) SEQUENCE DESCRIPTION: SEQ ID NO:1:

```
TCGCGATCTG ATCAACGATT CGTGGAATCT GGTGGTTGAT GGTCTGGCTA AACGCGATCA        60

AAAAAGAGTG CGTCCAGGCT AAAGCGGAAA TCTATAGCGC ATTTTTCTCG CTTACCATTT       120

CTCGTTGAAC CTTGTAATCT GCTGGCACGC AAAATTACTT TCACATGGAG TCTTT ATG       178
                                                            Met
                                                             1

GAT ATC ATT TCT GTC GCC TTA AAG CGT CAT TCC ACT AAG GCA TTT GAT         226
Asp Ile Ile Ser Val Ala Leu Lys Arg His Ser Thr Lys Ala Phe Asp
             5                  10                  15

GCC AGC AAA AAA CTT ACC CCG GAA CAG GCC GAG CAG ATC AAA ACG CTA         274
Ala Ser Lys Lys Leu Thr Pro Glu Gln Ala Glu Gln Ile Lys Thr Leu
         20                  25                  30

CTG CAA TAC AGC CCA TCC AGC ACC AAC TCC CAG CCG TGG CAT TTT ATT         322
Leu Gln Tyr Ser Pro Ser Ser Thr Asn Ser Gln Pro Trp His Phe Ile
     35                  40                  45

GTT GCC AGC ACG GAA GAA GGT AAA GCG CGT GTT GCC AAA TCC GCT GCC         370
Val Ala Ser Thr Glu Glu Gly Lys Ala Arg Val Ala Lys Ser Ala Ala
 50                  55                  60                  65

GGT AAT TAC GTG TTC AAC GAG CGT AAA ATG CTT GAT GCC TCG CAC GTC         418
Gly Asn Tyr Val Phe Asn Glu Arg Lys Met Leu Asp Ala Ser His Val
                 70                  75                  80

GTG GTG TTC TGT GCA AAA ACC GCG ATG GAC GAT GTC TGG CTG AAG CTG         466
Val Val Phe Cys Ala Lys Thr Ala Met Asp Asp Val Trp Leu Lys Leu
             85                  90                  95

GTT GTT GAC CAG GAA GAT GCC GAT GGC CGC TTT GCC ACG CCG GAA GCG         514
```

-continued

```
Val Val Asp Gln Glu Asp Ala Asp Gly Arg Phe Ala Thr Pro Glu Ala
        100                 105                 110

AAA GCC GCG AAC GAT AAA GGT CGC AAG TTC TTC GCT GAT ATG CAC CGT        562
Lys Ala Ala Asn Asp Lys Gly Arg Lys Phe Phe Ala Asp Met His Arg
    115                 120                 125

AAA GAT CTG CAT GAT GAT GCA GAG TGG ATG GCA AAA CAG GTT TAT CTC        610
Lys Asp Leu His Asp Asp Ala Glu Trp Met Ala Lys Gln Val Tyr Leu
130                 135                 140                 145

AAC GTC GGT AAC TTC CTG CTC GGC GTG GCG GCT CTG GGT CTG GAC GCG        658
Asn Val Gly Asn Phe Leu Leu Gly Val Ala Ala Leu Gly Leu Asp Ala
                150                 155                 160

GTA CCC ATC GAA GGT TTT GAC GCC GCC ATC CTC GAT GCA GAA TTT GGT        706
Val Pro Ile Glu Gly Phe Asp Ala Ala Ile Leu Asp Ala Glu Phe Gly
            165                 170                 175

CTG AAA GAG AAA GGC TAC ACC AGT CTG GTG GTT GTT CCG GTA GGT CAT        754
Leu Lys Glu Lys Gly Tyr Thr Ser Leu Val Val Val Pro Val Gly His
        180                 185                 190

CAC AGC GTT GAA GAT TTT AAC GCT ACG CTG CCG AAA TCT CGT CTG CCG        802
His Ser Val Glu Asp Phe Asn Ala Thr Leu Pro Lys Ser Arg Leu Pro
    195                 200                 205

CAA AAC ATC ACC TTA ACC GAA GTG TAATTCTCTC TTGCCGGGCA TCTGCCCGGC       856
Gln Asn Ile Thr Leu Thr Glu Val
210                 215

TATTTCCTCT CAGATTCTCC TGATTTGCAT AACCCTGTTT CAGCCGTCAT CATAGGCTGC      916

TGTTGTATAA AGGAGACGTT ATGCAGGATT TAATATCCCA GGTTGAAGAT TTAGCGGGTA      976

TTGAGATCGA TCACACCACC TCGATGGTGA TGATTTTCGG TATTATTTTT CTGACCGCCG     1036

TCGTGGTGCA TATTATTTTG CATTGGGTGG TACTGCGGAC CTTCGAAAAA CGTGCCATCG     1096

CCAGTTCACG GCTTTGGTTG CAAATCATTA CCCAGAATAA ACTCTTCCAC CGTTTAGCTT     1156

TTACCCTGCA G                                                          1167

(2) INFORMATION FOR SEQ ID NO:2:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Ile Ile Ser Val Ala Leu Lys Arg His Ser Thr Lys Ala Phe
 1               5                  10                  15

Asp Ala Ser Lys Lys Leu Thr Pro Glu Gln Ala Glu Gln Ile Lys Thr
            20                  25                  30

Leu Leu Gln Tyr Ser Pro Ser Ser Thr Asn Ser Gln Pro Trp His Phe
        35                  40                  45

Ile Val Ala Ser Thr Glu Glu Gly Lys Ala Arg Val Ala Lys Ser Ala
    50                  55                  60

Ala Gly Asn Tyr Val Phe Asn Glu Arg Lys Met Leu Asp Ala Ser His
65                  70                  75                  80

Val Val Val Phe Cys Ala Lys Thr Ala Met Asp Asp Val Trp Leu Lys
                85                  90                  95

Leu Val Val Asp Gln Glu Asp Ala Asp Gly Arg Phe Ala Thr Pro Glu
            100                 105                 110

Ala Lys Ala Ala Asn Asp Lys Gly Arg Lys Phe Phe Ala Asp Met His
        115                 120                 125

Arg Lys Asp Leu His Asp Asp Ala Glu Trp Met Ala Lys Gln Val Tyr
```

```
             130                 135                 140

Leu Asn Val Gly Asn Phe Leu Leu Gly Val Ala Ala Leu Gly Leu Asp
145                 150                 155                 160

Ala Val Pro Ile Glu Gly Phe Asp Ala Ala Ile Leu Asp Ala Glu Phe
                165                 170                 175

Gly Leu Lys Glu Lys Gly Tyr Thr Ser Leu Val Val Val Pro Val Gly
                180                 185                 190

His His Ser Val Glu Asp Phe Asn Ala Thr Leu Pro Lys Ser Arg Leu
            195                 200                 205

Pro Gln Asn Ile Thr Leu Thr Glu Val
        210                 215
```

(2) INFORMATION FOR SEQ ID NO: 3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
CGCAAAAAAG CTTTCACATT GAGTCATTAT GG                               32
```

(2) INFORMATION FOR SEQ ID NO: 4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CGGCAAGGGA TCCTTACACT TCGGTTAAGG TGATG                            35
```

BACTERIAL NITROREDUCTASE GENE-PRODRUG SYSTEM

FIELD OF INVENTION

The present invention relates to viral mediated gene therapy and its use in the treatment of tumours.

TECHNOLOGY BACKGROUND

A therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug only in the vicinity of the tumour cells (Huber et al, Proc. Natl. Acad. Sci. USA (1991) 88, 8039).

Although the VDEPT system enhances the concentrations of anti-tumour agent which may be delivered to the site of a tumour, there is still a need to enhance the specificity and efficiency of drug delivery.

The present invention addresses such problems by the use of a VDEPT viral vector which encodes for a nitroreductase.

SUMMARY OF THE INVENTION

The present invention therefore provides a system comprising:

(i) a viral vector comprising a nucleotide sequence encoding a nitroreductase, which nitroreductase is capable of converting a prodrug into a cytotoxic drug; and (ii) a prodrug capable of being converted into an active drug by the nitroreductase encoded by the vector.

The invention also provides a kit which comprises a vector defined herein together with a prodrug as defined herein.

In another aspect, the invention provides a system as defined herein or a kit as defined herein for use in a method of treatment of the human or animal body, and in particular a method of treatment of tumours.

In a further aspect, the invention provides a method of treatment of tumours which comprises administering to an individual with a tumour (i) an effective amount of a vector as defined herein, and (ii) an effective amount of a prodrug capable of being converted to an active drug by the nitroreductase encoded by the vector.

In a further embodiment, the invention provides a method of ablating normal tissue which comprises administering to a human or animal body an effective amount of a vector as defined herein and an effective amount of a prodrug capable of being converted to an active drug by a nitroreductase encoded by the vector.

In a further embodiment the invention provides a method for killing cells in an animal or human wherein a viral vector comprising a nucleic acid sequence encoding a nitroreductase which converts a prodrug into a cytotoxic drug is introduced into animal or human cells in vitro so that nitroreductase is produced in the cells, the cells are administered to an animal or human, and a prodrug is then administered to the animal or human, where it is converted into a cytotoxic agent in nitroreductase-containing cells of the animal.

In a further embodiment the invention provides a product containing a viral vector as defined herein and a prodrug as defined herein as a combined preparation for simultaneous, separate or sequential use in the treatment of tumours or the ablation of tissue.

BRIEF DESCRIPTION OF THE DRAWINGS

FIG. 3. Two graphs comparing the nitroreductase/CB 1954 and thymidine kinase/gancyclovir enzyme/prodrug systems. FIG. 3a shows that arrest of NTR-expressing NIH3T3 cells does not affect the relative cytotoxicity of increasing quantities of CB 1954, whereas

DETAILED DESCRIPTION OF THE INVENTION

Figure 1:
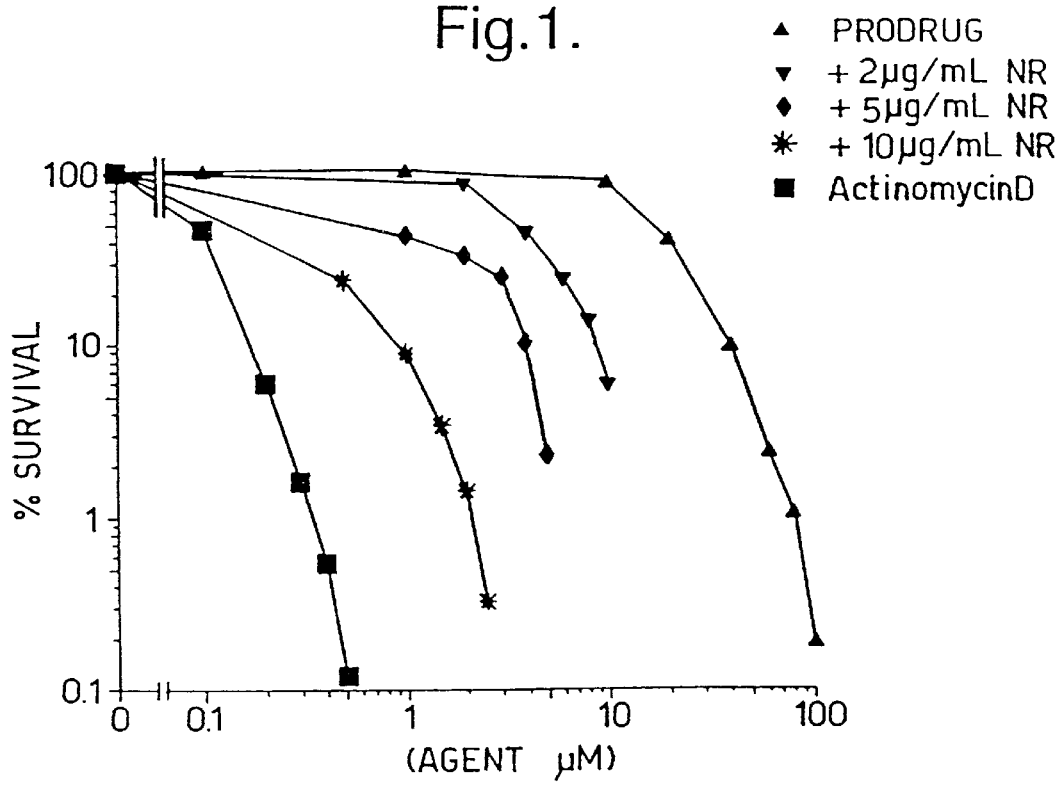
FIG. 1. Graph demonstrating the cytotoxicity achieved by the action of nitroreductase (NR) at various concentrations upon the N-4-nitrobenzyloxycarbonyl derivative (prodrug) of actinomycin D.

The viral vector may be any suitable vector available for targeting tumour cells, such as, for example, retroviral, adenoviral or virosomal vectors. Huber et al Proc., Natl. Acad. Sci. USA (1991), 88, 8039, report the use of amphotrophic retroviruses for the transformation of hepatoma, breast, colon or skin cells. Culver et al (Science (1992) 256; 1550–1552) also describe the use of retroviral vectors in VDEPT, as do Ram et al (Cancer Research (1993) 53; 83–88). Englehardt et al (Nature Genetics (1993) 4; 27–34) describe the use of adenovirus based vectors in the delivery of the cystic fibrosis transmembrane conductance product (CFTR) into cells.

Accordingly, any suitable RNA or DNA vector including vectors of the type mentioned above may be used in the preparation of a vector according to the invention. Those of skill in the art will be able to prepare vectors which will be modified by genetic engineering techniques known per se, such as those described by Sambrook et al (Molecular Cloning: A Laboratory Manual, 1989).

Preferably, the viral vector of the invention comprises a promoter operably linked to the gene encoding the nitroreductase. "Operably linked" refers to a juxtaposition wherein the promoter and the enzyme-coding sequence are in a relationship permitting the coding sequence to be expressed under the control of the promoter. Thus, there may be elements such as 5' non-coding sequence between the promoter and coding sequence which is not native to either the promoter or the coding sequence. Such sequences can be included in the vector if they do not impair the correct control of the coding sequence by the promoter. Suitable promoters include tissue and tumour specific promoters, such as, for example, the promoter for milk protein, the CEA gene promoter or the CA-125 gene promoter. Promoters for milk protein include the CHβ promoter, preferably from sheep, the β-lactoglobulin (BLG) promoter, the α-lactalbumin promoter and the whey acidic protein promoter.

Although it is preferred to include in the vector a native mammalian or human promoter sequence, modified promoter sequences which are capable of selectively hybridizing to the mammalian or human sequence may be included in the vector. A promoter sequence capable of selectively hybridizing to the human promoter sequence will be generally at least 70%, preferably at least 80 or 90% and more preferably at least 95% homologous to the promoter region or fragment thereof over a region of at least 20, preferably at least 30, for instance 40, 60 or 100 or more contiguous nucleotides.

In general, those of skill in the art will appreciate that some regions of promoters will need to be retained to ensure tissue specificity of expression from the vector whereas other regions of the promoter may be modified or deleted without significant loss of specificity.

For use of the vectors in therapy, the vectors will usually be packaged into viral particles and the particles delivered to the site of the tumour, as described in for example Ram et al (ibid). The particles may be delivered to the tumour by any suitable means at the disposal of the physician. For example, parenterally. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution.

The nitroreductase of the system of the invention includes fragments and homologues thereof which retain the nitroreductase activity. A nitroreductase according to the invention is an enzyme capable of reducing a nitro group to the corresponding hydroxylamino group in various compounds.

The gene encoding the nitroreductase preferably comprises the oligonucleotide of the sequence shown in SEQ ID NO: 1, a fragment thereof or oligonucleotide hybridisable thereto. An oligonucleotide capable of hybridising to the oligonucleotide of SEQ ID NO: 1 or fragment thereof will generally be at least 70%, preferably at least 80 or 90% and more preferably at least 95% homologous to the oligonucleotide of SEQ ID NO: 1 or fragment thereof over a region of at least 20, preferably at least 30, for example 40, 60 or 100 or more contiguous nucleotides. The sequence of the oligonucleotide may be varied by deleting at least one nucleotide, inserting at least one nucleotide or substituting at least one nucleotide in the sequence.

The oligonucleotides may be RNA or DNA. The oligonucleotide fragments typically will be at least 10, for example at least 20, 30, 40, 60 or 100 nucleotides long.

The nitroreductase encoded by the vector is preferably bacterial nitroreductase, for example a nitroreductase which is a flavoprotein having a molecular weight in the range 20 to 60 kDa, which requires NADH or NAD(P)H or analogues thereof as a cofactor and which has a Km for NADH or NAD(P)H in the range 1 to 100 μM such as that described in EP-A-540 263. Typically the nitroreductase is the same as that from *E. coli,* Salmonella or Clostridia organisms.

Preferably the nitroreductase of the invention is a nitroreductase having the sequence of SEQ ID No: 2, a fragment thereof or homologue thereof.

A nitroreductase of SEQ. ID No. 2 in substantially purified form will generally comprise the protein in a preparation in which more than 90%, eg. 95%, 98% or 99% of the protein in the preparation is that of the SEQ. ID No. 2.

A homologue of the SEQ. ID No. 2 will be generally at least 70%, preferably at least 80 or 90% and more preferably at least 95% homologous to the protein of SEQ. ID No. 2 over a region of at least 20, preferably at least 30, for instance 40, 60 or 100 or more contiguous amino acids.

Generally, fragments of SEQ. ID No. 2 or its homologues will be at least 10, preferably at least 15, for example 20, 25, 30, 40, 50 or 60 amino acids in length. The sequence of the polypeptide may be varied by deleting, inserting or substituting at least one amino acid.

The prodrug which will be used in conjunction with the vector of the invention will be a compound which can be converted by the nitroreductase encoded by the vector into a cytotoxic drug. Desirably, the toxicity of the prodrug to the patient being treated will be at least one order of magnitude less toxic to the patient than the active drug. Preferably, the cytotoxic drug will be several, eg 2, 3, 4 or more orders of magnitude more toxic.

Suitable prodrugs include nitrogen mustard compounds and other compounds such as those described in WO93/08288 or EP-A-540 263. Preferred prodrugs are compounds of the general formula:

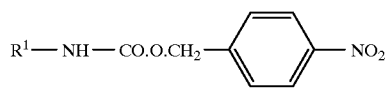

I and:

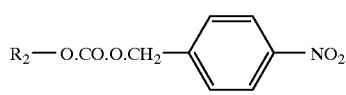

II where $R^1$ and $R^2$ are groups such that the compound $R^1NH_2$ and $R^2OH$ are cytotoxic compounds.

It is preferred that compounds $R^1NH_2$ and $R^2OH$ are aromatic cytotoxic compounds and the compounds $R^1NH_2$ can be any one of the well known nitrogen mustard compounds, for example based on p-phenylene diamine. Thus, the compound $R^1NH_2$ can be:

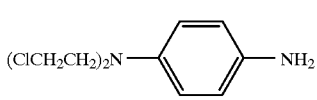

III or analogues of this compound with the general structure IV

IV

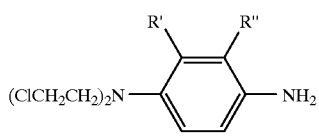

where R' and R" are H, F or CH₃, and particularly where
R'=H and R"=CH₃;
or R'=CH₃ and R"=H;
or R'=H and R"=F;
or R'=F and R"=H.

Further types of amino cytotoxic compounds that can be used in accordance with the present invention are compounds such as actinomycin D, and mitomycin C. The structure of the pro-drugs derived from actinomycin D and mitomycin C are shown below as V and VII respectively.

V

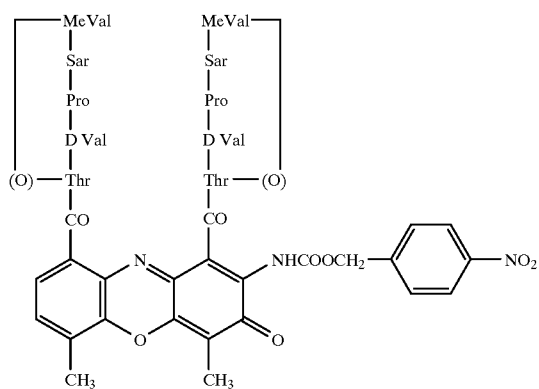

VII

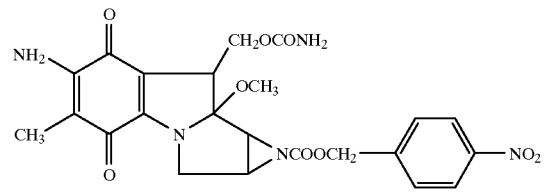

Similar p-nitrobenzyloxy derivatives can be made at the amino substituent of other actinomycins and of the other cytotoxic compounds of the type mentioned above.

In addition to forming p-nitrobenzyloxycarbonyl derivatives at an amino group on a cytotoxic compound, similar derivatives can be made at a hydroxy group, particularly a phenolic hydroxy group of a cytotoxic compound. Here, attention is directed at the phenolic nitrogen mustard compounds, and the compound of formula VIII:

VIII

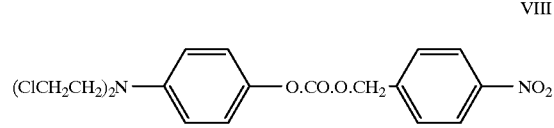

Suitable prodrugs also include other aromatic nitro compounds such as 5-chloro-2,4-dinitrobenzamide, 3,5-dinitrobenzamide, 3-nitrobenzamide, 4-nitrobenzamide and 5-nitro-2-furfuraldehydesemicarbazone (nitrofurazone).

Particularly preferred prodrugs are CB 1954 (5-(aziridin-1-yl)-2,4-dinitrobenzamide), SN 23862 (5-(bis(2'-chloroethyl)amino)-2,4-dinitrobenzamide) and analogues of CB 1954 or SN 23862, such as those described in WO 93/11099 or, for example descarboxamido CB 1954 (1-aziridin-1-yl-2,4-dinitrobenzamide—known as CB 1837), N,N-dimethyl CB 1954 (N,N-dimethyl-(5-aziridin-1-yl)-2,4-dinitrobenzamide—known as CB 10-107), CB 10-199, CB 10-200, CB 10-201, CB 10-217, CB 10-021 and CB 10-214.

CB 10-199

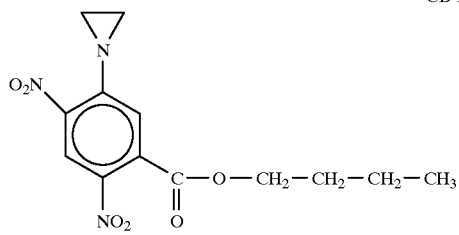

CB 10-200

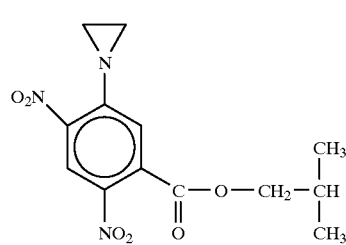

CB 10-201

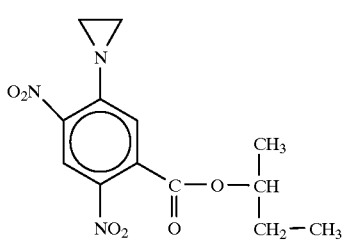

CB 1837

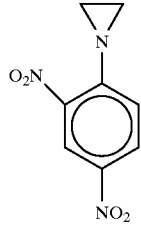

CB 10-217

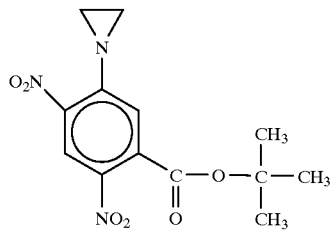

-continued

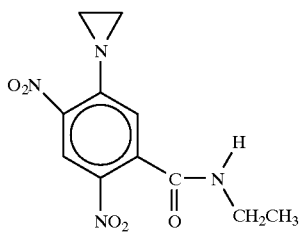
CB 10-021

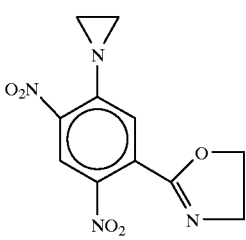
CB 10-214

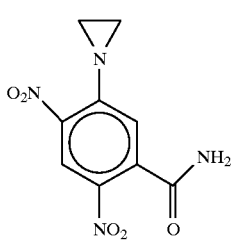
CB 1954

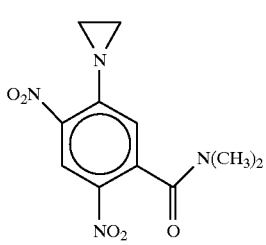
CB 10-107

The prodrugs which may be used in the system of the present invention generally comprise a cytotoxic drug linked to a suitable protecting group. Generally the protecting group is removable by a nitroreductase as defined herein or is converted into another substituent by a nitroreductase as defined herein. Alternatively the prodrug is converted by the nitroreductase directly to an active form. In the case of CB1954 and its analogues the active form is a mixture of the 2- and 4-hydroxylamino derivatives. These are formed in equal proportions by the nitroreductase (Knox et al, Biochem. Pharmacol 44: 2297–2301, 1992). In the case of the 4-hydroxylamine (5-(aziridin-1-yl)-4-hydroxylamino-2-nitrobenzamide) this can become a species capable of binding to DNA and producing interstrand crosslinks, by a direct, non-enzymatic, reaction with either acetyl coenzyme A, butyl and propyl coenzyme A or S-acetylthio-choline. It is thought that the ultimate, DNA reactive species of this derivative of CB 1954 is 4-(N-acetoxy)-5-(aziridin-1-yl)-2-nitrobenzamide (Knox et al, Biochem. Pharmacol 42: 1691–1697, 1991). In the case of SN 23862 only a single product is produced by the nitroreductase and this is the 2-hydroxylamine. This hydroxylamine can also be activated to a DNA crosslinking agent by a direct reaction with a thioester.

The prodrugs of the system of the invention are conveniently prepared by methods of chemical synthesis. For example p-nitrobenzyloxycarbonyl compounds are conveniently prepared by methods of chemical synthesis. For example, the amine or hydroxy cytotoxic compounds can be reacted with 4-nitrobenzyl chloroformate under anhydrous conditions in the presence of a hydrogen chloride acceptor, particularly an alkylamine such as triethylamine. This reaction can be carried out in a dry organic solvent such as chloroform and the resulting compound isolated from the organic solvent by conventional methods such as chromatography.

The prodrug may include any suitable group which can be removed by or modified by a nitroreductase defined herein in such a manner that the group is unstable and undergoes "self immolation" to provide the cytotoxic drug.

Nitroreductases of the present invention are capable of reducing a nitro group in various substrate molecules and we have found that the nitroreductases are particularly useful in their ability to reduce the nitro group of various p-nitrobenzyloxycarbonyl derivatives of cytotoxic compounds to give "self-immolative" compounds that automatically decompose to release cytotoxic compounds. Generally the nitroreductase reduces the nitro group to the corresponding hydroxylamino group.

The interest in the present approach resides in the fact that the various cytotoxic compounds containing amino or hydroxy substituents, particularly aromatic amino or hydroxy substituents, give rise to p-nitrobenzyloxycarbonyl derivatives of the amino or hydroxy group which exhibit considerably less cytotoxicity than the amino or hydroxy parent compound. Thus, it is possible to use the p-nitrobenzyloxycarbonyl derivatives as prodrugs in a system of the type discussed above where the prodrug is converted into an anti-tumour agent under the influence of a polypeptide expressed within a tumour cell.

For example, compounds of formula (I)

$$R^1\text{—NH—CO.O—CH}_2\text{—Ph—NO}_2 \qquad (I)$$

where Ph is a phenylene ring and R' is a group such that $R^1\text{-NH}_2$ is a cytotoxic compound; and (II)

$$R^2\text{—O—CO.O—CH}_2\text{—Ph—NO}_2 \qquad (II)$$

where Ph is as defined above and $R^2$ is a group such that $R^2\text{—OH}$ is a cytotoxic compound may be used as prodrugs in a VDEPT system in conjunction with a nitroreductase defined herein, including the *E.coli* nitroreductase described in WO93/08288. While the present invention is not dependent, for its definition, upon the exact mode of action of the nitroreductase on the prodrug, for compounds of formula I or II, it is believed that the nitro group of the p-nitrophenyl-benzyloxy-carbonyl residue is converted to the corresponding hydroxylamino group and that the resulting p-hydroxyl-aminobenzyloxycarbonyl compound automatically degrades under the reaction conditions used for the enzymatic reduction to release the cytotoxic compound and form p-hydroxylaminobenzyl alcohol and carbon dioxide as by products in accordance with the following reaction scheme:

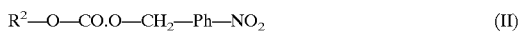
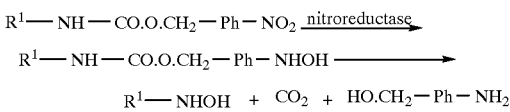

(Mauger et al J. Med. Chem. 1994 vol 37. p3452–3458).

For use in VDEPT, all types of prodrug should preferably be able to enter cells. Accordingly, modifications may be made in the prodrug, eg to make the prodrug more or less lipophilic.

In order to bring about the reduction of the prodrug with the nitroreductase described herein, it is necessary to have a cofactor present in the reaction system. Nitroreductase requires NAD(P)H as cofactor. Since NAD(P)H has a very short serum half-life, concentrations in the blood stream are very low. Accordingly, any nitroreductase produced according to the system of the invention which is released into the blood stream by cell lysis will be unable to activate any circulating prodrug owing to the absence of NAD(P)H. Thus the presence or absence of cofactor allows a greater selectivity of the VDEPT system so that prodrug is activated only within cells.

In VDEPT the prodrug will usually be administered following administration of the modified virus encoding a nitroreductase. Typically, the virus will be administered to the patient and then the uptake of the virus by infected cells monitored, for example by recovery and analysis of a biopsy sample of targeted tissue.

The exact dosage regime for VDEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and modified virus and administration by the intravenous route is frequently found to be the most practical.

The vector of the system of the invention may be administered to animals or humans by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-indicated utilities and indications the amount required of the individual active ingredients will depend upon a number of factors including the severity of the condition to be treated and the identity of the recipient and will ultimately be at the discretion of the attendant physician. In general, however, for each of these utilities and indications, a suitable, effective dose will be in the range 1 $\mu$g to 10 g per kilogram body weight of recipient per day, preferably in the range 0.01 to 100 mg per kilogram body weight per day and most preferably in the range 0.1 to 10 mg per kilogram body weight per day. The dose may, if desired, be presented as two, three, four or more sub-doses administered at appropriate intervals throughout the day. These sub-doses may be administered in unit dosage forms, for example, containing 1 $\mu$g to 1000 mg, preferably 0.01 to 100 mg and most preferably 0.1 to 10 mg of active ingredient per unit dosage form.

While it is possible for the compounds to be administered alone it is preferable to present them as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

The formulations may be applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Injection solutions and suspensions may be prepared extemporaneously from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The prodrug of the system of the invention may also be administered to an animal or human by any of the means stated herein, in any of the formulations stated herein and in the dosage rates stated herein.

Examples of tumours that can be treated by the system of the invention are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, and ovarian carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, gliomas and retinoblastomas.

According to a further embodiment of the invention, the viral vector is incorporated into a cell, such as, for example, a fibroblast, prior to administration to a patient. The gene may be introduced into the cell using standard techniques, such as, for example, calcium phosphate or electroporation. In this case targeting is achieved by the restriction of viral insertion to those cells synthesising DNA. It is also envisaged that targeting could be achieved by using antibodies to specific tumours. Unlike Antibody Directed Enzyme Prodrug Therapy the antibody would be internalised. However the nature of virosomes are such that they are then targeted towards the cell nucleus and circumvent the compartmentalisation and breakdown normally associated with insertion.

The system of the present invention may be used to ablate normal tissue, for example breast tissue, particularly in women who are shown to have the "breast-cancer gene", or to ablate specific normal cells in animals for studies on normal tissue development (pharmacogenics).

The prodrugs of the system of the invention, which are converted to active form by nitroreductase, are cyctotoxic to non-cycling cells as well as to cycling cells.

DETAILED DESCRIPTION OF THE PREFERRED EMBODIMENTS

The present invention is illustrated by means of the following Examples.

EXAMPLE 1

The effect of CB 1954 on the survival of V79 cells in the presence of the *E. coli* nitroreductase is shown in Table I. All treatments were for 2 hours at 37° C. and the cells were then plated out for their resulting colony forming ability. NADH was used as a co-factor for both enzymes.

TABLE I

| TREATMENT | % SURVIVAL | % DRUG REDUCTION |
|---|---|---|
| CONTROL | 100 | — |
| +500 µM NADH | 100 | — |
| +50 µM CB 1954 | 100 | <1.0 |
| +NADH + CB 1954 | 41 | <1.0 |
| +Nitroreductase (2 µg/ml) | 94 | — |
| +NR + 50 µM CB 1954 | 99 | <1.0 |
| +NR + 50 µM CB 1954 + 500 µM NADH | 0.024 | 72 |

EXAMPLE 2

The effect of SN23862 on the survival of V79 cells in the presence of the *E. coli* nitroreductase. All treatments were for 2 hours at 37° C. and the cells were then plated out for their resulting colony forming ability. The nitroreductase concentration was 2 µg/ml and NADH was used as a co-factor. The initial cell density was $2\times10^5$/mL.

TABLE II

| TREATMENT | % SURVIVAL | % DRUG REDUCTION |
|---|---|---|
| CONTROL | 100 | — |
| +500 µM NADH | 100 | — |
| +50 µM SN23862 | 100 | <1.0 |
| +NADH + SN23862 | 100 | <1.0 |
| +Nitroreductase (2 µg/mL) | 94 | — |
| +NR + 50 µM drug | 99 | <1.0 |
| +NR + SN23862 + 500 µM NADH | 0.007 | 95 |

EXAMPLE 3

Generation of cytotoxicity by the action of NR upon the N-4-nitrobenzyloxycarbonyl derivative of actinomycin D (AMD)

Various concentrations of the prodrug were incubated with 1 mL of V79 cells ($2\times10^5$/mL), NADH (500 µL) and NR (2, 5 or 10 µg/mL) in PBS. After 2 h at 37° C., the cells were harvested and assayed for colony forming ability. The results are shown in FIG. 1, from which it can be seen that the cytotoxicity of the prodrug is greatly enhanced in the presence of NR and is dependent on the concentration of the enzyme.

EXAMPLE 4

Cytoxicity of CB 1954 Towards Nitroreductase Transduced NIH3T3 Cells

Figure 2:
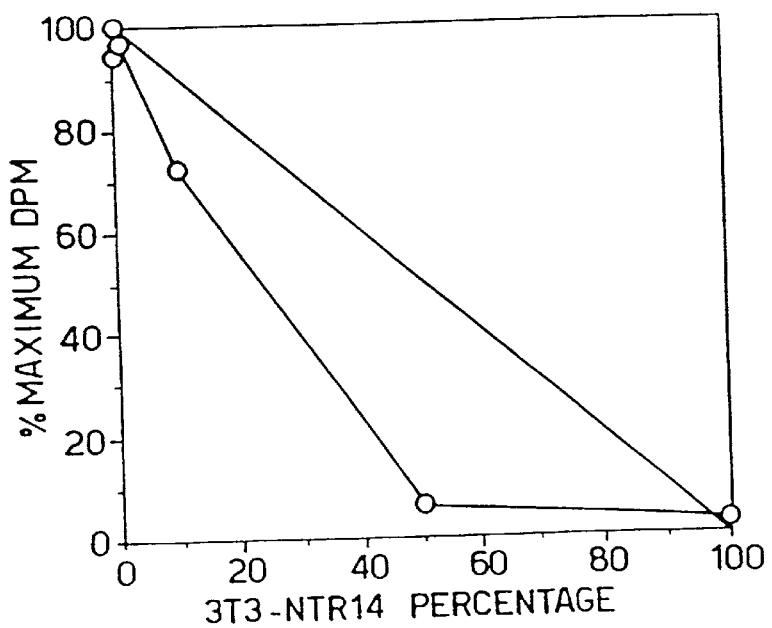
FIG. 2. Graph demonstrating the bystander effect and cytotoxicity achieved by CB 1954 administration to nitroreductase-transduced NIH3T3 cells as observed with a standard thymidine-incorporation assay. Results are plotted as the quantity of $^3$H-thymidine incorporation into live cells (10% decays/min) (Y-axis) versus the percentage of transduced cells in the sample population (X-axis).

As suggested by the observation that the bulk infected, unselected cell population could be efficiently killed, a bystander effect was seen when 3T3-NTR14 cells were mixed with untransduced NIH3T3 cells. FIG. 2 shows that 90% inhibition of $^3$H-thymidine incorporation (shown as 10% decays/minute) could be achieved with only 50% transduced cells.

EXAMPLE 5

Figure 3A:
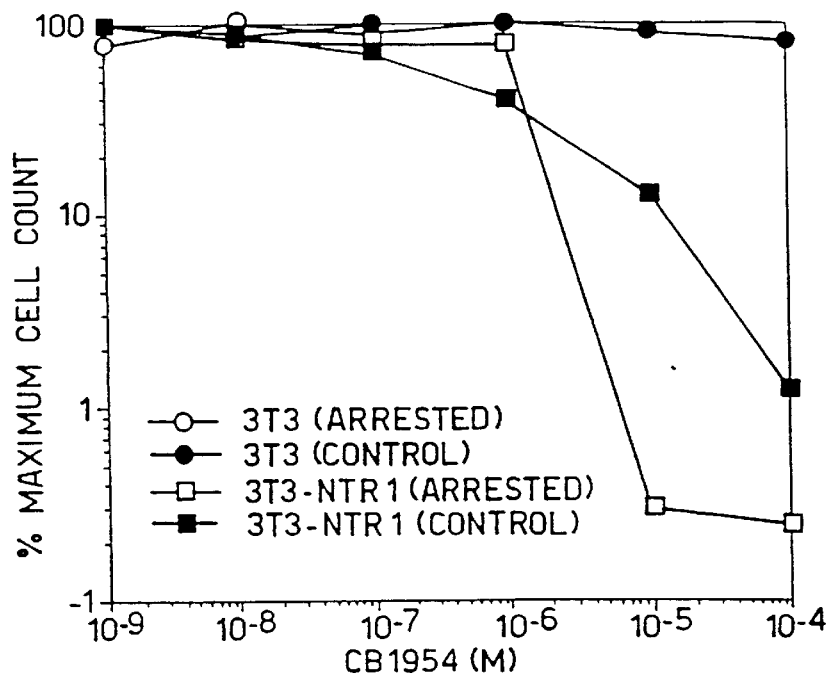
Figure 3B:
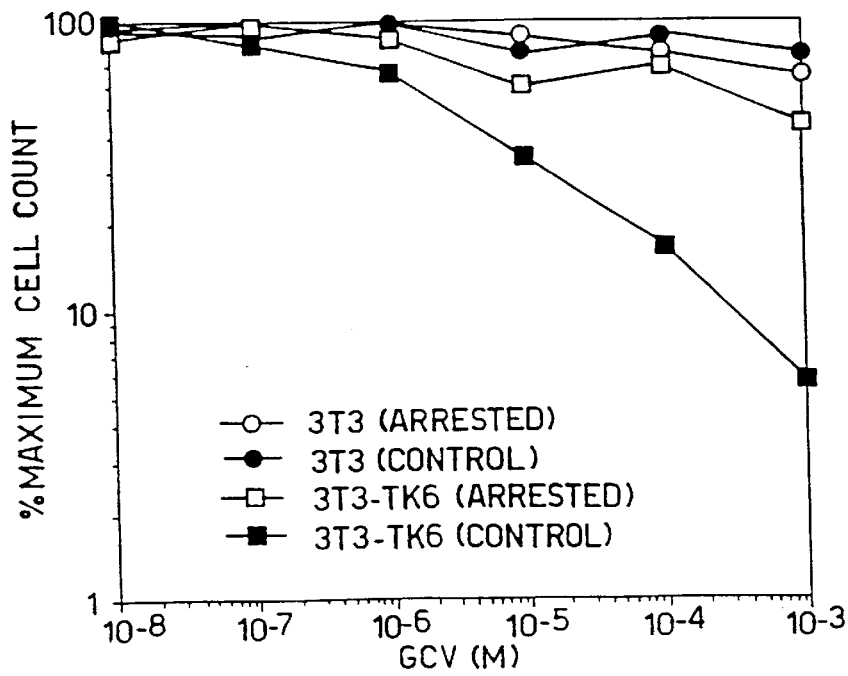
FIG. 3b shows that arrest of TK-expressing NIH3T3 cells prevents gancyclovir (GCV) cytotoxicity over a wide range of drug concentrations ($10^{-8}$ to $10^{-3}$ M)

Comparison of the Nitroreductase/CB 1954 and Thymidine Kinase/Ganciclovir Enzyme/Prodrug Systems Cells must be in S-phase for cytotoxic GCV-triphosphate incorporation into DNA, whereas activated CB 1954, which acts as a cross linking agent does not require active cell division for cytotoxicity. Indeed, arrest of NTR-expressing NIH3T3 cells by serum deprivation does not affect their killing by CB 1954 (FIG. 3a), whereas similar arrest of TK-expressing NIH3T3 cells prevents GCV killing (FIG. 3b).

EXAMPLE 6

In vitro Expression of Nitroreductase (NR) in Breast Epithelial Cells a) Cloning Nitroreductase Two primers were used to amplify the coding region from a plasmid supplied by the Public Health Laboratory Service (PHLS), and designated NTR1003.

The sense primer is: 5'CGCAAAAAAGCTTTCACAT-TGAGTCATTATGG3' (SEQ ID NO 3)

This was designed to add a HindIII site, knock out an upstream ATG, and improve the initiation site for translation in mammalian cells.

The antisense primer is:

5'C G G C A A G G G AT C C T TA C A C T T C G G T-TAAGGTGATG3' (SEQ ID NO 4)

This was designed to add a BamHI site. The coding region was amplified using Pfu polymerase, and the HindIII-BamHI fragment was directionally cloned into pREP8 (Invitrogen). A clone with the correct restriction map was sequenced from the RSV enhancer region to confirm that the 5' end of the clone was correct and was designed NRR8/3. pREP8 and pNRR8/3 were transfected into E.coli NFR-343 (lacking nitroreductase), and ampicillin resistant colonies were selected for assay. pREP8 and pR8NR were purified for mammalian cell transfections using "Qiagen" reagents.

b) Expression of Nitroreductase In Epithelial Cells

HB4a, an SV40 conditionally immortalised human breast (lumenal) cell line was transfected with pREP8 and pNRR8/3 using calcium phosphate precipitation, and stable transfectants selected under 1 mM Histidinol. For each plasmid 50–60 drug resistant colonies were obtained which were then pooled and continuously maintained under selection.

Figure 4:
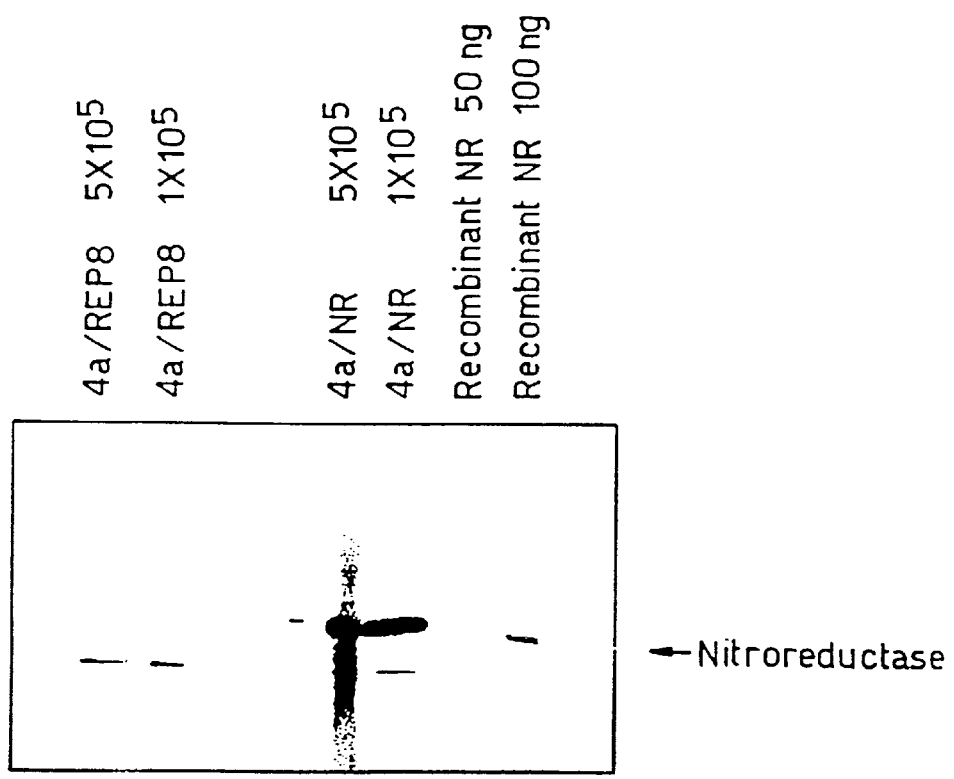
FIG. 4. Immunoblot of whole cell lysates from HB4a cells transfected with either pREP8 or pNTR8/3 using a rabbit polyclonal antibody, rb 6s4/ntr.

The pooled populations of HB4a/REP8 and HB4a/NR were expanded and examined for nitroreductase protein expression. Immunoblotting of whole cell lysates using a rabbit polyclonal antibody, rb 6s4/ntr, showed HB4a/NR to express large amounts of nitroreductase protein which bands at the appropriate weight as compared to recombinant E.coli nitroreductase protein (FIG. 4). As expected HB4a/REP8 did not express any nitroreductase protein.

c) Enzymatic Reduction of CB 1954

CB 1954 (100 $\mu$M) and NADH (500 $\mu$M) were incubated with a cell lysate prepared by sonication (250 $\mu$l, 1 mg/mL protein) in 10 mM sodium phosphate buffer (pH7) at 37° C. At various times aliquots (10 $\mu$l) were injected onto a Partisphere SCX (110×4.7 mm) HPLC column and eluted isocratically (2 ml/min) with 50 mM NaH$_2$PO$_4$ in 1% (v/v) methanol. The eluate was continuously monitored for absorption at 260, 310, 340 nm using a diode-array detector. Alternatively, [U-$^3$H]CB 1954 was added to give an activity of 1.6×10$^5$ dpm per nmole). Samples (0.3 ml) were collected and their tritium activity determined by liquid scintillation counting. Protein concentration was determined by a standard method (Biorad), calibrated against bovine albumin.

d) Determination of cell survival

Cells were trypsinised and resuspended in fresh media at 2×10$^5$ cells per mL. They were then treated for two hours with CB 1954 (10 $\mu$l of appropriate stock in DMSO). The treated cells were then spun down, washed with fresh media, and plated out in triplicate at various concentrations. Cells were fixed and stained after 14 days incubation at 37° C. in a humidified atmosphere of 5% CO$_2$ and 95% air.

e) Expression in HOSPIP cells

The modified gene described above was ligated into the vectors pREP4 and pREP8. These two vectors with high level constitutive transcription from the RSV LTR have Hygromycin and Histidinol selectable markers respectively for coexpression of recombinant proteins. Both of these constructs have been transfected into the rat mammary carcinoma cell line HOSPIP by the calcium phosphate technique and are currently under appropriate selection conditions to isolate resistant clones.

f) Determination of DNA interstrand crosslinks

HB4a/NR cells were radiolabelled by growth for 48 hours in [$^3$h]-thymidine. The cells were then treated with either 0, 10 or 50 $\mu$M CB 1954 for 24 hours and their DNA then analysed by sedimentation in alkaline sucrose.

Results

Enzymatic Reduction of CB 1954

Figure 5:
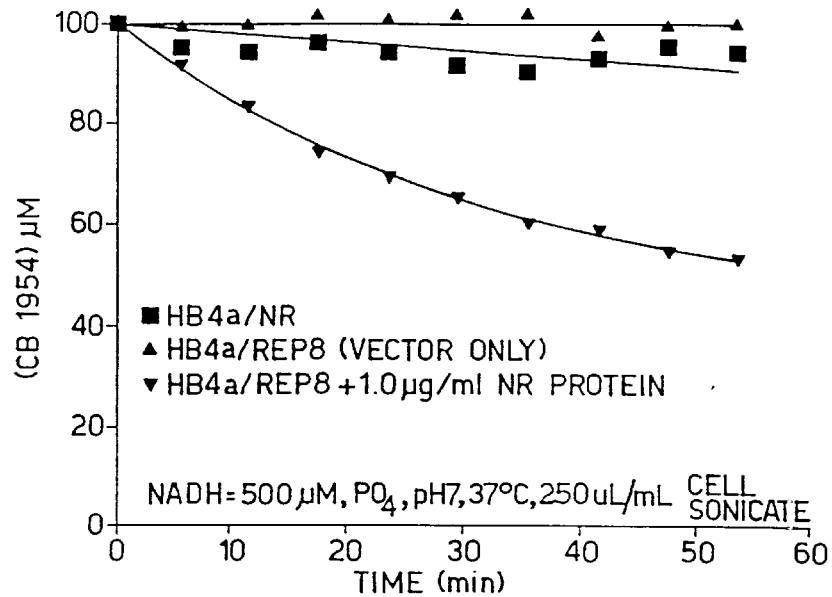
FIG. 5. Graph demonstrating a time-dependent decrease in the concentration of CB 1954 in the presence of HB4a/NR cells as compared with HB4a/REP8 cells with and without pure NR protein.
Figure 6:
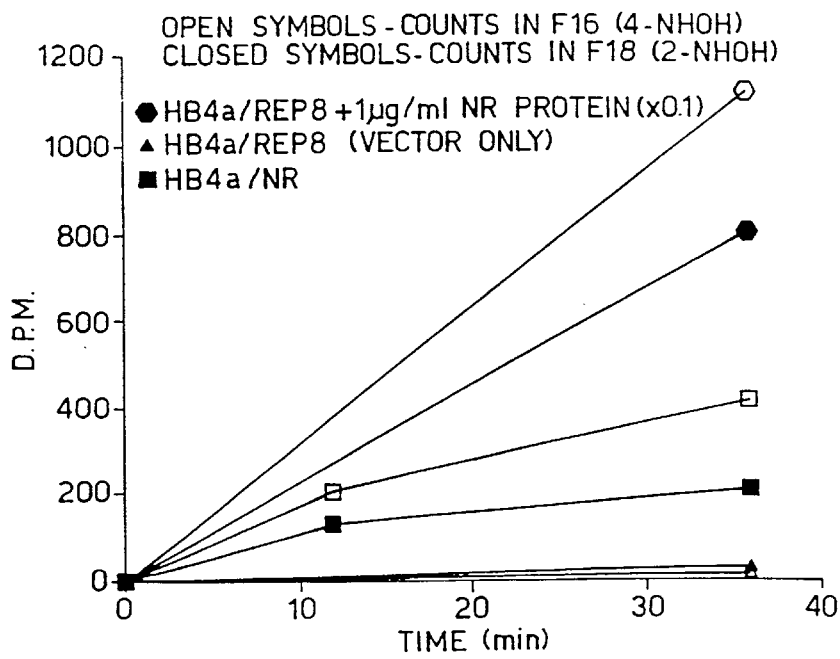
FIG. 6. Graph demonstrating the quantity of radiolabelled 2- and 4-hydroxylamino reduction products (2-NHOH and 4-NHOH) of CB 1954 over time in the presence of HB4a/NR, HB4a/REP8 and HB4a/REP8 in the presence of 1 $\mu$g/ml pure NR protein.

HB4a/NR cells but not HB4a/REP8 cells showed a time dependent decrease in the concentration of CB 1954 (FIG. 5). Examination of the traces also indicated the formation of the 2- and 4-hydroxylamino reduction products of CB 1954. This was confirmed by the use of radiolabelled prodrug (FIG. 6). The protein concentration of the HB4a/NR lysate in the assay mixture was determined to be 0.3 mg/mL and the enzyme activity estimated to be 0.05 $\mu$g/mL by comparison with the pure protein (see FIGS. 5 and 6). Thus NR activity is 1.7 $\mu$g/mg cell protein (~1.7 $\mu$g/10$^6$ cells).

Cell Survival

The plating efficiency of both the HB4a/NR and HB4a/REP8 cell lines was poor and cells only grew when plated at a high initial cell density (1×10$^4$ per dish). These plates were scored by eye for cell growth. Results are shown in Table III. There is a dramatic difference in cell survival between the two cell lines. After a 2 hour exposure the HB4a/NR line exhibits cytotoxicity at 1.0 $\mu$M while the HB4a/REP8 line shows no cytotoxicity until the dose is >100 $\mu$M.

DNA Crosslinked Formation

Figure 7A:
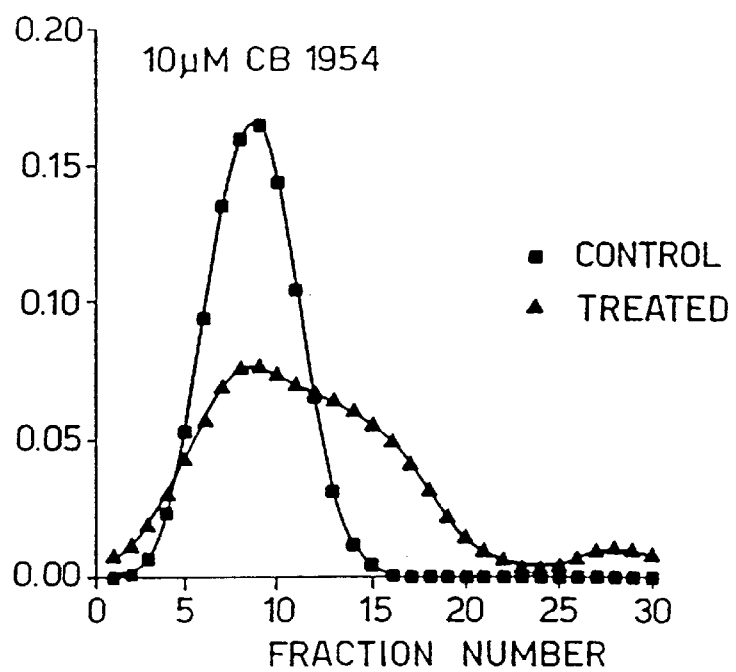
FIG. 7. Graphs demonstrating increased formation of DNA interstrand crosslinks in the presence of 10 $\mu$M CB 1954 (FIG. 7a) and 50 $\mu$M CB 1954 (FIG. 7b) as indicated by the increasing proportion of DNA of higher molecular weight which sediments further into the alkaline sucrose gradient.
Figure 7B:
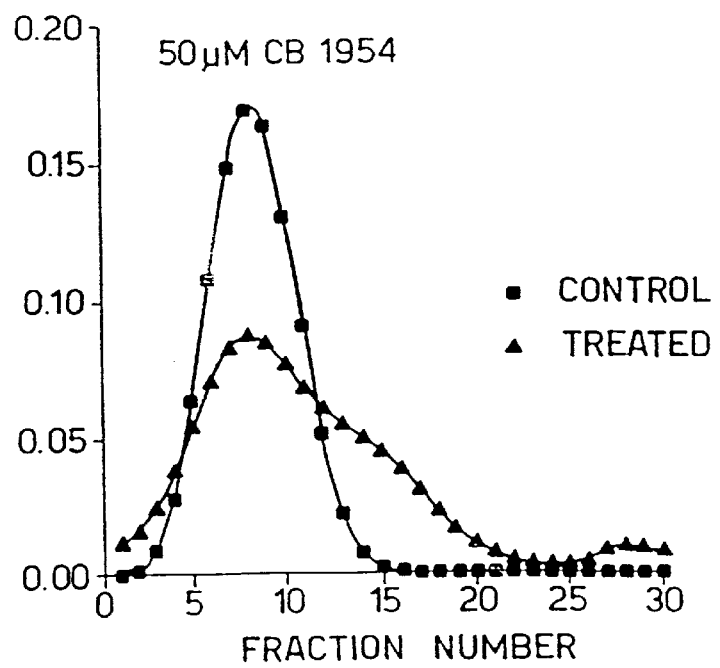

Confirmation that the cyctotoxicity of CB 1954 in HB4a/NR cells is due to its enzymic reduction is obtained by demonstrating the ability of this compound to form DNA interstrand crosslinks (FIG. 7). Increasing amounts of CB 1954 produce a progressive increase in the amount of DNA that is crosslinked as indicated by the increasing proportion of DNA of higher molecular weight which sediments further into the alkaline sucrose gradient (sedimentation is from left to right) (FIG. 7). DNA strand breakage (either frank breaks or alkali labile sites) is also observed and for clarity the sedimentation profiles are shown relative to a modelled control of the same molecular weight as the strand-broken experimental DNA. 10 μM CB 1954 produces about 6 crosslinks and 25 breaks per $10^9$ daltons of DNA whilst 50 μM CB 1954 produces 12 crosslinks and 28 breaks. These effects are not seen in untreated cells.

TABLE III

The effect of CB 1954 on the survival of human HB4a/NR or HB4a/REP8 cell lines. All treatments were for 2 hours at 37° C.

| [CB 1954] μM | 4A/Rep | 4A/NR |
|---|---|---|
| 0.0 | +++ | +++ |
| 1.0 | +++ | +-- |
| 10 | +++ | --- |
| 100 | +++ | --- |
| 1000 | --- | --- |

We claim:

1. A two component virally directed enzyme prodrug system, comprising:

(i) a viral vector comprising a nucleotide sequence encoding a bacterial nitroreductase operably linked to a promoter, wherein the nitroreductase coverts a prodrug into a cytotoxic drug; and (ii) a prodrug which is converted into a cytotoxic drug by the nitroreductase.

2. The system according to claim 1, wherein the nitroreductase is that of SEQ ID NO: 2, or a fragment thereof having nitroreductase activity.

3. The system according to claim 1, wherein the cytotoxic drug kills both dividing and non-dividing cells.

4. The system according to claim 1, wherein the viral vector is a viral particle.

5. The system according to claim 1, wherein the prodrug is a nitrogen mustard compound.

6. The system according to claim 1, wherein the prodrug is selected from the group consisting of 5-(aziridin-1-yl)-2,4-dinitrobenzamide and 5-(bis(2'-chloroethyl)amino)-2,4-dinitrobenzamide.

7. A method of killing a cell comprising:

(i) transfecting the cell in vitro with a viral vector comprising a nucleotide sequence encoding a bacterial nitroreductase operably linked to a promoter and expressing the nucleotide sequence;

(ii) introducing to the transfected cells a prodrug which is converted into a cytotoxic drug by the nitroreductase; and (iii) incubating the transfected cells of step (ii) such that the cell is killed.

8. The method according to claim 7, wherein the prodrug is a nitrogen mustard compound.

9. The method according to claim 7, wherein the prodrug is selected from the group consisting of 5-(aziridin-1-yl)-2,4-dinitrobenzamide and 5-(bis(2'-chloroethyl)amino)-2,4-dinitrobenzamide.

10. The method according to claim 7, wherein the nitroreductase is that of SEQ ID NO: 2, or a fragment having nitroreductase activity.

11. A method of killing cancer cells in vitro comprising:

(i) mixing or introducing said cancer cells in vitro with cells comprising a nucleotide sequence encoding a bacterial nitroreductase operably linked to a promoter and expressing the nucleotide sequence;

(ii) introducing to the cells of step (i) a prodrug which is converted into a cytotoxic drug by the nitroreductase;

(iii) incubating the transfected cells of step (ii) such that the susceptibility of the cancer cell to death by the cytotoxic drug is increased over that of cancer cells not incubated with cells comprising the nucleotide sequence.

12. The method according to claim 11, wherein the prodrug is a nitrogen mustard compound.

13. The method according to claim 11, wherein the prodrug is selected from the group consisting of 5-(aziridin-1-yl)-2,4-dinitrobenzamide and 5-(bis(2'-chloroethyl)amino)-2,4-dinitrobenzamide.

14. The method according to claim 11, wherein the nitroreductase is that of SEQ ID No: 2, or a fragment thereof having nitroreductase activity.

* * * * *